US00PP12690P2

(12) United States Plant Patent
Fruehwirth

(10) Patent No.: US PP12,690 P2
(45) Date of Patent: Jun. 11, 2002

(54) POINSETTIA PLANT NAMED 'ECKADATI'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/432,712

(22) Filed: Nov. 2, 1999

(51) Int. Cl.[7] ..... A01H 5/00
(52) U.S. Cl. ..... Plt./303

(58) Field of Search ..... Plt./303

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Eckadati', characterized by its red and pink variegated bracts; early flowering, response time about 8 weeks; dark green leaves; compact and upright plant habit; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckadati'.

The new Poinsettia is a product of a mutation induction breeding program conducted by the Inventor in Encinitas, Calif. The objective of the Inventor's Poinsettia development program is to create new Poinsettia cultivars having interesting bract and leaf display, desirable bract and foliage color and form, strong and freely branching stems and good post-production longevity.

The new Poinsettia originated by exposing unrooted cuttings of the *Euphorbia pulcherrima* Willd. cultivar Pepride, disclosed in U.S. Plant Pat. No. 10,183, to gamma-ray rediation at a level of 3,000 rads. The new Poinsettia was discovered and selected by the Inventor in December, 1997. The selection of this plant was based on its unique variegated bract color.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckadati'. These characteristics in combination distinguish 'Eckadati' as a new and distinct cultivar:

1. Red and pink variegated bracts.
2. Early flowering, response time about 8 weeks.
3. Dark green leaves.
4. Compact and upright plant habit.
5. Excellent postproduction longevity.

In side-by-side comparisons conducted in Encinitas, Calif., plants of the new Poinsettia and the parent cultivar Pepride differ primarily in bract coloration as Pepride has bright red-colored bracts. In addition, plants of the new Poinsettia are more compact, have smaller leaves, and have smaller inflorescences with few bracts than plants of 'Pepride'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckadati'.

The photograph at the bottom top of the first sheet comprises a top perspective view of a typical plant of 'Eckadati'.

The photograph on the second sheet is a close-up view of typical bracts and leaves of 'Pepride' (left) and 'Eckadati' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures ranging from 21 to 27° C., night temperatures ranging from 18 to 20° C., and light levels about 4,000 foot-candles. Plants were grown in 16-cm pots. pinched one time, and flowered under naturally lengthening nyctoperiods during the fall/early winter.

In the following description, color references are made to The Royal Horticultural Society Colour Chart except where general terms of ordinary dictionary significance are used.

Botanical classification: *Euphorbia pulcherrima* Willd. 'Eckadati'.

Parentage: Induced mutation of *Euphorbia pulcherrima* Willd. cultivar Pepride, disclosed in U.S. Plant Pat. No. 10,183.

Propagation:

*Type cutting*.—Terminal cuttings.

*Time to initiate roots*.—Summer: About 7 days at 24° C. Winter: About 10 days at 22° C.

*Time to develop roots*.—Summer: About 26 days at 24° C. Winter: About 26 days at 22° C.

*Rooting habit*.—Freely branching, becoming fibrous with development.

Plant description:

*Plant form*.—Inverted triangle.

*Growth habit*.—Upright and compact. Branching is enhanced by removing the shoot apex. Moderately vigorous.

*Plant height*.—About 20 cm.

*Crop time*.—From unrooted cutting to a flowering plant in a 16-cm container, about 16 weeks are required.

*Stem description*.—Number of lateral branches: About five lateral branches are formed after removal of the terminal apex. Lateral branch length: About 10 cm. Internode length: About 8 mm. Stem color: 146A.

*Foliage description*.—Quantity of leaves per lateral branch: About 7. Length: About 9.5 cm. Width: About 4.75 cm. Shape: Mostly narrowly ovate with irregular pointed lobes. Apex: Acuminate. Base: Rounded acute. Margin: Entire. Texture: Rugose; curled; very sparse pubescence on lower surface. Color: Young foliage, upper surface: Mostly darker than 139A with random areas of lighter green, 137A. Young foliage, lower surface: Mostly 139B with random areas of lighter green, 137C to 137D. Mature foliage, upper surface: Darker than 139A. Mature foliage, lower surface: 137A. Venation, upper surface: 137C. Venation, lower surface: 137D. Petiole: Length: About 3.25 cm. Diameter: About 2 mm. Color: 60 A.

Inflorescence description:

*Inflorescence type and habit*.—Inflorescences are compound corymbs of cyathia with colored flower bracts subtending the cyathia.

*Natural flowering season*.—Autumn/winter in Northern Hemisphere. Flower initiation and development can be induced under long nyctoperiod conditions. Response time is about 8 weeks.

*Quantity of inflorescences*.—One per lateral branch, usually about five per plant.

*Inflorescence size*.—Diameter: About 20 cm. Height (depth): About 4.5 cm.

*Flower bracts*.—Quantity of flower bracts per inflorescence: Usually about 12 primary bracts and about 6 smaller secondary bracts per inflorescence. Length, largest bracts: About 10 cm. Width, largest bracts: About 7 cm. Shape: Mostly ovate with irregular pointed lobes. Apex: Acuminate. Base: Acute. Margin: Entire. Texture: Rugose. Aspect: Mostly horizontal. Color: Random red and pink variegation patterns. Developing, upper surface: Background, 45A to 45B, with irregular areas of 52A. Developing, lower surface: Background, 45B, with irregular areas of 52B. Mature, upper surface: Background, more cherry red than 45B, with irregular areas of 51C. Mature, lower surface: Background, slightly brighter than 53B, with irregular areas of 51C and 51D.

*Cyathia*.—Quantity: Usually about 9 per corymb. Diameter of cyathia cluster: About 2 by 2.5 cm. Length: About 9 mm. Width: About 5 mm. Color: Immature: 144B. Mature: 144A. Peduncle: Length: About 3 mm. Aspect: Strong, erect. Color: 144B. Stamens: Stamen number: Five to ten with numerous stamenoids per cyathium. Anther length: About 1 mm. Anther shape: Oval. Anther color: 46A. Amount of pollen: Very scarce. Pollen color: 7A. Pistils: No pistillate flowers observed. Nectary color: 21A.

Disease resistance: Plants of the new Poinsettia have been observed to be resistant to Botrytis.

Postproduction longevity: Excellent; generally plants maintain good substance and bract color for about eight weeks under interior conditions.

It is claimed:

1. A new and distinct cultivar of Poinsettia plant named 'Eckadati', as illustrated and described.

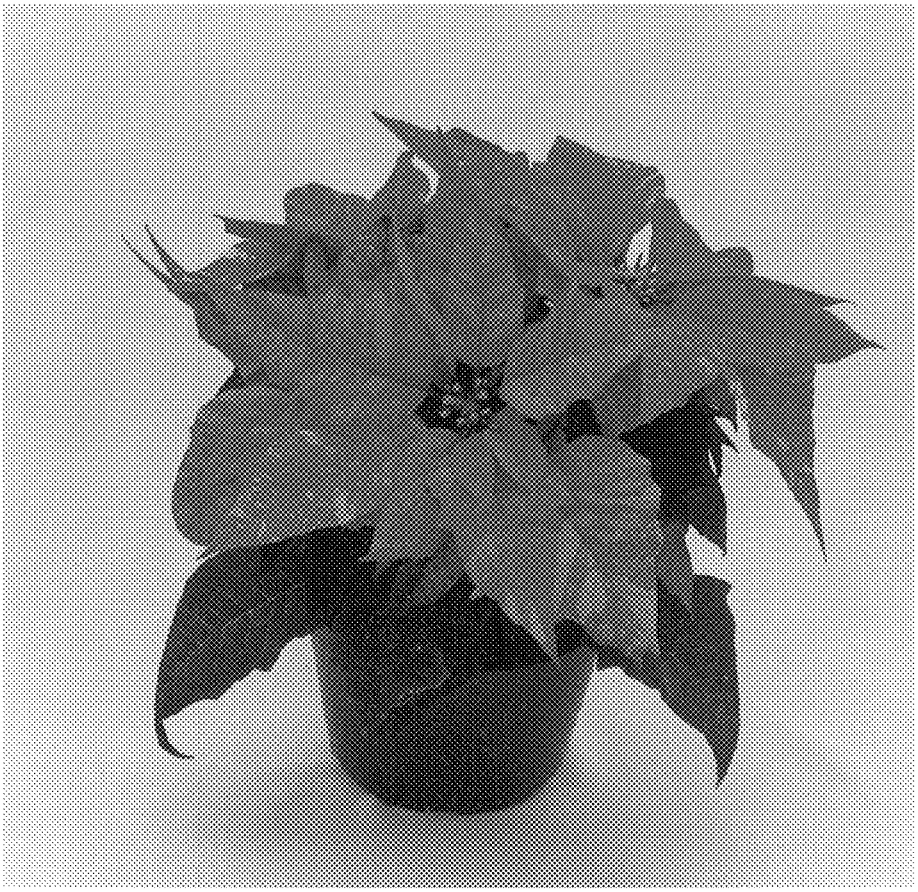
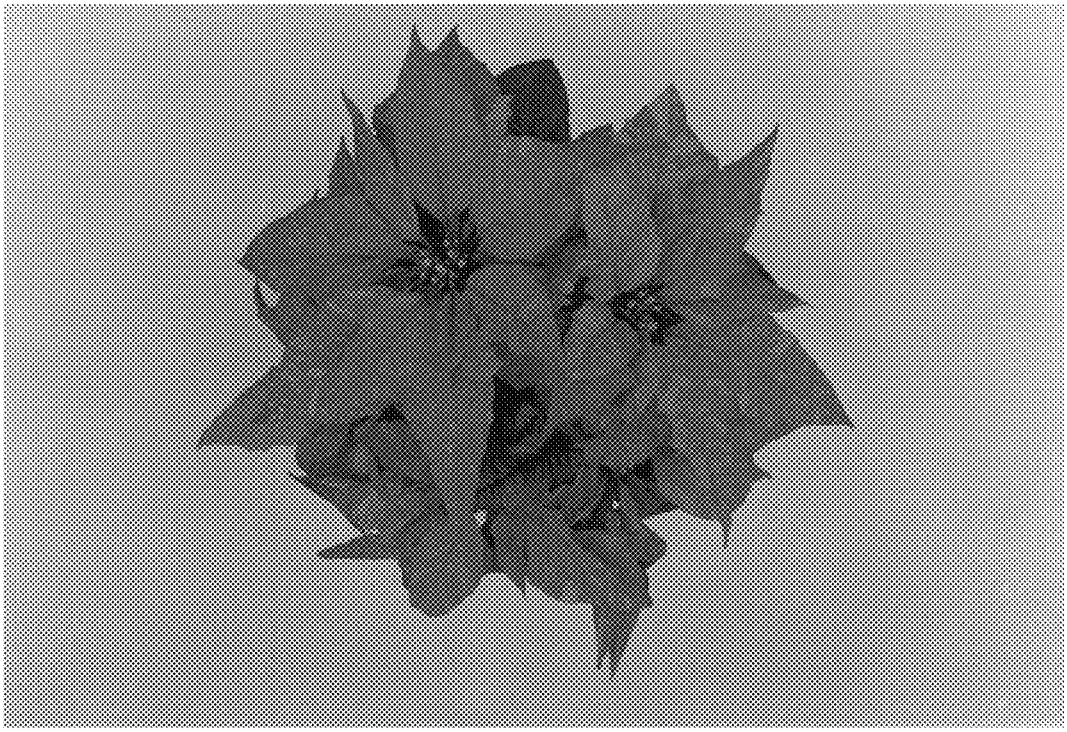

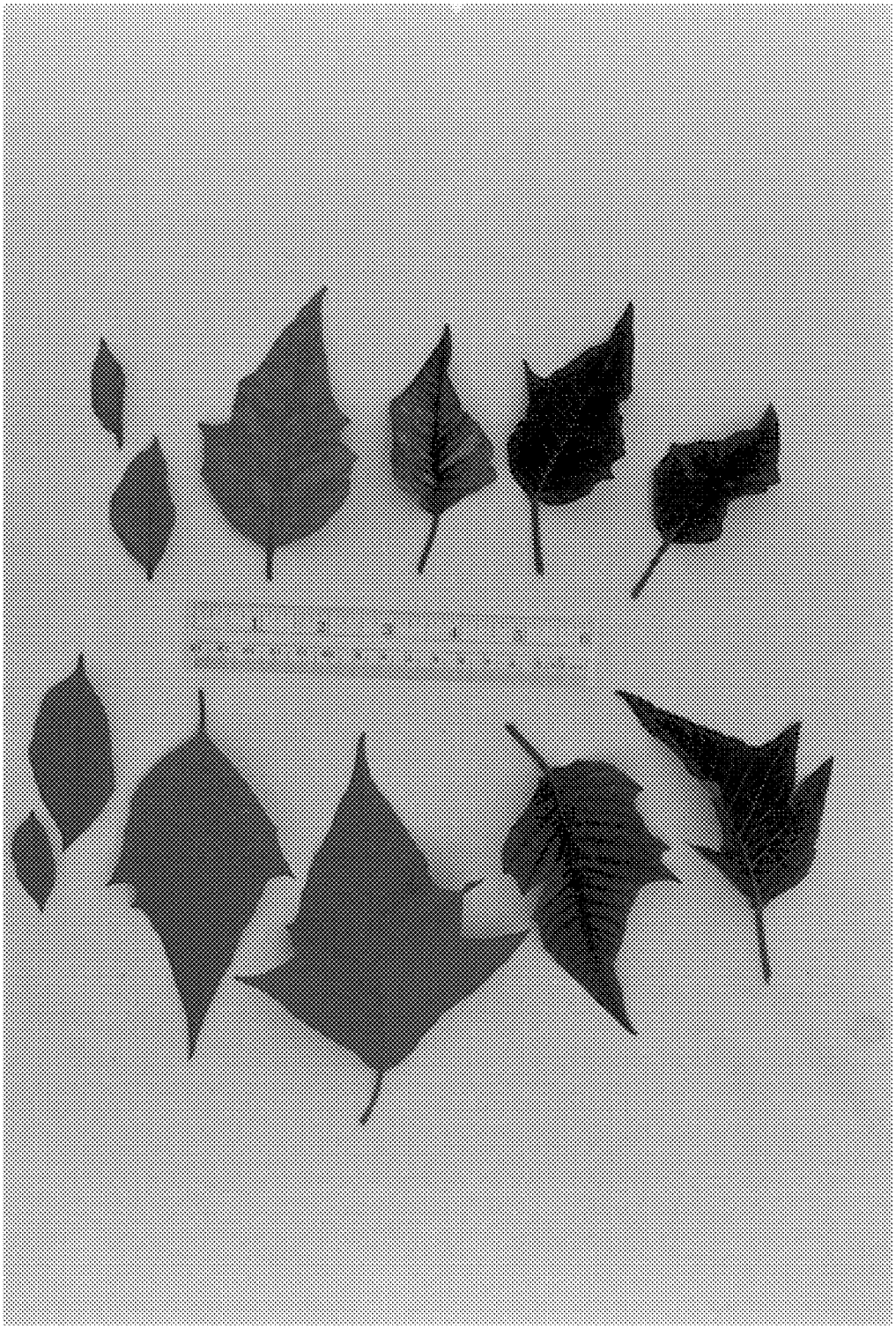

* * * * *